United States Patent
Damodaran et al.

(10) Patent No.: US 12,376,799 B2
(45) Date of Patent: Aug. 5, 2025

(54) SIGNAL-TO-NOISE RATIO TARGETING

(71) Applicant: KONINKLIJKE PHILIPS N.V., Eindhoven (NL)

(72) Inventors: Mathi Damodaran, 'S-Hertogenbosch (NL); Yannyk Parulian Julian Bourquin, Eindhoven (NL); Jonathan Alambra Palero, Waalre (NL); Rieko Verhagen, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 192 days.

(21) Appl. No.: 17/925,037

(22) PCT Filed: Jun. 8, 2021

(86) PCT No.: PCT/EP2021/065307
§ 371 (c)(1),
(2) Date: Nov. 14, 2022

(87) PCT Pub. No.: WO2021/250007
PCT Pub. Date: Dec. 16, 2021

(65) Prior Publication Data
US 2023/0181118 A1    Jun. 15, 2023

(30) Foreign Application Priority Data

Jun. 10, 2020 (EP) .................................... 20179192

(51) Int. Cl.
*H04N 23/75*    (2023.01)
*A61B 5/00*    (2006.01)

(52) U.S. Cl.
CPC .... *A61B 5/7203* (2013.01); *A61B 2560/0247* (2013.01)

(58) Field of Classification Search
CPC .................. A61B 5/7203; A61B 2560/0247
(Continued)

(56) References Cited

U.S. PATENT DOCUMENTS

2010/0002093 A1    1/2010    Arai et al.
2013/0057713 A1    3/2013    Khawand
(Continued)

FOREIGN PATENT DOCUMENTS

CN    101247479 A    8/2008
CN    101247480 A    8/2008
(Continued)

OTHER PUBLICATIONS

Anonymous: "How to Change Lighting for Different Skin Tones", Aug. 8, 2019, (Aug. 8, 2019), XP055729747, Retrieved from the Internet: https://www.tumblestonphotography.com/2019/08/08/how-to-change-lighting-for-different-skin-tones/ [retrieved on Sep. 10, 2020].
(Continued)

*Primary Examiner* — Nguyen T Truong (57) ABSTRACT

In an embodiment, a method (100) is described. The method comprises receiving (102) data corresponding to an ambient-corrected image of a subject illuminated by an illumination unit (206) providing temporally modulated illumination with a modulation frequency that is higher than a frame acquisition rate used by an imaging device (204) to obtain a set of images having a different spatial intensity modulation pattern in each image. The ambient-corrected image is constructed from the obtained set of images. The method (100) further comprises determining (104) a signal-to-noise ratio, SNR, of at least a portion of the ambient-corrected image. In response to determining that the SNR is below a target SNR, the method causes (106) an indication of an illumination parameter to be sent to the illumination unit to increase an amplitude modulation depth of the temporally modulated illumination used to illuminate the subject while the imaging device acquires a subsequent set of images for constructing a subsequent ambient-corrected image.

15 Claims, 5 Drawing Sheets

(58) Field of Classification Search
USPC .......................................................... 348/46
See application file for complete search history.

(56) References Cited

U.S. PATENT DOCUMENTS

2015/0098709 A1  4/2015  Breuer et al.
2019/0306413 A1  10/2019 Liu et al.

FOREIGN PATENT DOCUMENTS

| CN | 106210471 A   | 12/2016 |
| CN | 107888908 A   | 4/2018  |
| EP | 2947482 A2    | 11/2015 |
| EP | 2947482 A3    | 11/2015 |
| JP | 2010157925 A1 | 7/2010  |
| WO | 2012175703 A1 | 12/2012 |
| WO | 2021089422 A1 | 5/2021  |
| WO | 2021165035 A1 | 8/2021  |

OTHER PUBLICATIONS

Texas Instruments, OPT3001 Ambient Light Sensor (ALS), SBOS681C—Jul. 2014—Revised Nov. 2017, 1. http://www.ti.com/lit/ds/symlink/opt3001.pdf.
International Search report and Written Opinion of PCT/EP2021/065307, dated Jul. 16, 2021.

SIGNAL-TO-NOISE RATIO TARGETING

CROSS-REFERENCE TO PRIOR APPLICATIONS

This application is the U.S. National Phase application under 35 U.S.C. § 371 of International Application No. PCT/EP2021/065307, filed on Jun. 8, 2021, which claims the benefit of European Patent Application No. 20179192.8, filed on Jun. 10, 2020. These applications are hereby incorporated by reference herein.

FIELD OF THE INVENTION

The invention relates to a method, apparatus and tangible machine-readable medium for use in imaging in certain conditions.

BACKGROUND OF THE INVENTION

A topic of interest in the field of non-obtrusive measurement and monitoring relates to skin sensing for personal care and health applications. Skin sensing systems are being developed that promise skin quantification and monitoring of features in the skin that may offer users information that is too small to detect, too faint to notice or too slow to follow. To deliver results that are acceptable to users, such skin sensing systems may need to provide sensitivity and specificity when performing skin sensing. Providing measurements taken by such skin sensing systems are proven to be robust and reliable, users may establish trust in these skin sensing systems.

Imaging-based skin sensing systems may need to determine information that could be affected by difficult-to-control parameters such as variations in ambient lighting. For example, certain uncontrolled environments such as at a user's home may feature undefined and/or potentially varying ambient lighting. Such uncontrolled environments may lead to erroneous measurements of a user's skin, which may, in turn, lead to unacceptable or untrusted results for the user. The imaging performance of some cameras (such as smartphone cameras) used in some imaging-based skin sensing systems may be variable such that the imaging data is unpredictable or unreliable.

Imaging-based skin sensing systems may implement various image processing techniques in order to determine certain information about the user's skin and/or the ambient lighting conditions. Certain ambient lighting conditions may affect the results obtained using certain image processing techniques, which may lead to compromised or inconsistent measurements of a user's skin.

SUMMARY OF THE INVENTION

Aspects or embodiments described herein relate to improving imaging in certain conditions. Aspects or embodiments described herein may obviate one or more problems associated with certain image processing techniques which may be affected by certain ambient lighting conditions.

In a first aspect, a method is described. The method is a computer-implemented method. The method comprises receiving data corresponding to an ambient-corrected image of a subject illuminated by an illumination unit. The illumination unit provides temporally modulated illumination. The temporally modulated illumination has a modulation frequency that is higher than a frame acquisition rate used by an imaging device to obtain a set of images. The set of images have a different spatial intensity modulation pattern in each image due to the temporally modulated illumination and the imaging device operating in a rolling shutter mode. Information from the obtained set of images is used to construct the ambient-corrected image. The effect of ambient lighting is reduced in the ambient-corrected image. The method further comprises determining a signal-to-noise ratio, SNR, of at least a portion of the ambient-corrected image. In response to determining that the SNR is below a target SNR, the method further comprises causing an indication of an illumination parameter to be sent to the illumination unit to increase an amplitude modulation depth of the temporally modulated illumination used to illuminate the subject while the imaging device acquires a subsequent set of images. The subsequent set of images are used for constructing a subsequent ambient-corrected image with increased SNR for at least a portion of the subsequent ambient-corrected image.

In a second aspect, a method is described. The method is a computer-implemented method. The method comprises receiving data corresponding to an ambient-corrected image of a subject illuminated by temporally modulated illumination. The ambient corrected image reduces the effect of ambient lighting caused by a light source. The method further comprises determining a signal-to-noise ratio, SNR, of at least a portion of the ambient-corrected image. Where the determined SNR is below a target SNR, the method further comprises providing an indication of an illumination parameter for achieving the target SNR for at least the portion of the image.

Certain embodiments relating to the first and/or second aspect are described below.

In some embodiments, the target SNR is based on a skin type of the subject.

In some embodiments, the target SNR is linked to a factor, A, for which a plurality of different skin types are associated with obtaining images with at least the target SNR. The factor, A, is defined as the ratio of ambient light level incident on the subject to a total amount of light incident on the subject. The total amount of light refers to the combination of the ambient light level and a modulation depth of amplitude modulation provided by the illumination unit. The indication is configured to change the modulation depth in dependence on the skin type to obtain the same factor, A, for each of the different skin types.

In some embodiments, the indication is configured to control an ambient light level for the subject to increase the SNR for at least the portion of the subsequent ambient-corrected image.

In some embodiments, the indication is configured to cause a decrease in the ambient light level to increase the SNR for at least the portion of the ambient-corrected image.

In some embodiments, the indication of the illumination parameter comprises a control instruction for specifying the ambient light level to be provided by a source of the ambient light.

In some embodiments, the method comprises using the indication to control a power supply for the source so that the specified ambient light level is provided.

In some embodiments, the indication of the illumination parameter comprises an instruction to indicate that a specified ambient light level is needed and/or a user action is needed to provide the specified ambient light level.

In some embodiments, the method further comprises causing the imaging device to acquire the set of images of the subject while the subject is illuminated by the temporally modulated illumination. The method may further comprise determining the ambient corrected image based on the set of images of the subject.

In some embodiments, the method further comprises causing the imaging device to acquire the subsequent set of images of the subject while the subject is illuminated by the temporally modulated illumination with increased amplitude modulation depth. The method may further comprise determining the subsequent ambient corrected image based on the subsequent set of images of the subject.

In some embodiments, before receiving the data corresponding to the ambient-corrected image, the method comprises selecting an initial amplitude modulation depth of the temporally modulated illumination and/or an initial ambient light level based on a skin type of the subject.

In a third aspect, a tangible machine-readable medium is described. The tangible machine-readable medium stores instructions which, when executed by at least one processor, cause the at least one processor to implement the method according to any preceding aspect or embodiment.

In a fourth aspect, apparatus is described. The apparatus comprises processing circuitry. The processing circuitry comprises a receiving module, a determining module and an indicating module. The receiving module is configured to receive data corresponding to an ambient-corrected image of a subject illuminated by an illumination unit providing temporally modulated illumination with a modulation frequency that is higher than a frame acquisition rate used by an imaging device to obtain a set of images. The set of images have a different spatial intensity modulation pattern in each image due to the temporally modulated illumination and the imaging device operating in a rolling shutter mode. Information from the obtained set of images is used to construct the ambient-corrected image. The effect of ambient lighting is reduced in the ambient-corrected image. The determining module is configured to determine a signal-to-noise ratio, SNR, of at least a portion of the ambient-corrected image. The indicating module is configured to cause, in response to determining that the SNR is below a target SNR, an indication of an illumination parameter to be sent to the illumination unit to increase an amplitude modulation depth of the temporally modulated illumination used to illuminate the subject while the imaging device acquires a subsequent set of images. The subsequent set of images are used for constructing a subsequent ambient-corrected image with increased SNR for at least a portion of the subsequent ambient-corrected image.

In a fifth aspect, apparatus is described. The apparatus comprises processing circuitry. The processing circuitry comprises a receiving module to receive data corresponding to an ambient-corrected image of a subject illuminated by temporally modulated illumination. The ambient corrected image reduces the effect of ambient lighting caused by a light source. The processing circuitry further comprises a determining module to determine a signal-to-noise ratio, SNR, of at least a portion of the ambient-corrected image. The apparatus further comprises an indicating module to provide, where the determined SNR is below a target SNR, an indication of an illumination parameter for achieving the target SNR for at least the portion of the image.

Certain embodiments relating to the fourth and/or fifth aspect are described below.

In some embodiments, the apparatus further comprises a control module for controlling: the illumination unit for providing the temporally modulated illumination; and/or a source of ambient light.

In some embodiments, the apparatus further comprises a user interface for providing an instruction, based on the indication of the illumination parameter, to indicate that a specified ambient light level is needed and/or a user action to provide the specified ambient light level.

These and other aspects of the invention will be apparent from and elucidated with reference to the embodiment(s) described hereinafter.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

Figure 1:
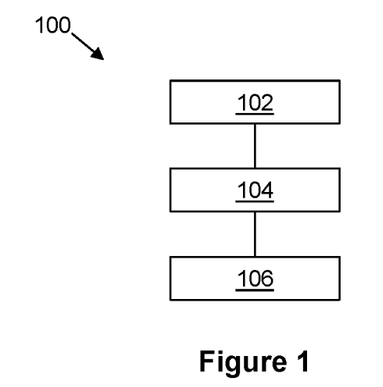
FIG. 1 refers to a method of improving imaging in certain conditions according to an embodiment.

FIG. 1 shows a method 100 (e.g., a computer-implemented method) of improving imaging in certain conditions. The method 100 may be implemented by a computer such as a user device, or a server or cloud-based service (e.g., communicatively coupled to the user device). An example of the user device includes a smart device such as a smartphone, tablet, smart mirror or any other device capable of displaying an image or a representation of an image of a subject.

The method 100 comprises, at block 102, receiving data corresponding to an ambient-corrected image of a subject illuminated by an illumination unit providing temporally modulated illumination with a modulation frequency that is higher than a frame acquisition rate used by an imaging device to obtain a set of images. The obtained set of images have a different spatial intensity modulation pattern in each image due to the temporally modulated illumination and the imaging device operating in a rolling shutter mode. Information from the obtained set of images is used to construct the ambient-corrected image. The effect of ambient lighting is reduced in the ambient-corrected image. The ambient-corrected image may be obtained by acquiring the set images of the subject and implementing a technique, using the spatial intensity modulation pattern in each image, to reduce the effect of ambient lighting caused by a light source (or multiple light sources) such as a room light or sunlight.

Block 102 refers to an example technique to reduce the effect of ambient lighting caused by a light source that comprises acquiring a set of images (e.g., at least three images) of the subject while temporally modulating (e.g., via periodic temporal modulation) the intensity of illumination provided by an illumination unit for illuminating the subject. An imaging device for acquiring the set of images operates in a rolling shutter mode (or another mode that involves acquiring different spatial portions of the image at different times within a frame) at a frame acquisition rate that is less than a modulation frequency of the temporally modulated illumination (e.g., in one example, for a frame rate of 30 frames per second (fps), the modulation frequency may be at least 70 Hz). In other similar words, the modulation frequency is higher than a frame acquisition rate used to obtain the set of images for constructing the ambient-corrected image. This means that as the imaging device acquires each image, the subject is illuminated at a varying intensity level while the imaging device performs its scan so that certain pixels of the imaging device register a higher intensity level than other pixels of the image device. As a result, each successive image of the set of images may have a different spatial intensity modulation pattern. The information from this set of images may be used to reconstruct an ambient-corrected image with the ambient light removed, normalized or at least reduced. In other similar words, the subject may appear to be evenly illuminated or without an apparent variation in ambient lighting across the surface of the subject's skin in the ambient-corrected image.

As mentioned above, in block 102, the method 100 refers to receiving data corresponding to an ambient-corrected image. This data may refer to data stored in a memory (such as of the computer implementing the method 100 or another memory) or data obtained after implementing a technique for reducing the effect of ambient lighting in an image. In other similar words, the computer for implementing the method 100 may have access to the memory storing the data and/or may itself implement the technique for reducing the effect of ambient lighting in an image.

The method 100 comprises, at block 104, determining a signal-to-noise ratio, SNR, of at least a portion of the ambient-corrected image.

The portion of the ambient-corrected image may refer to any area of the image. In some embodiments, multiple portions of the ambient-corrected image may be selected and the SNR of those multiple portions may be determined.

In some embodiments, the SNR may be defined by the following formula:

$$SNR = 10 * \log_{10}\left[\frac{\text{mean intensity}}{\text{standard deviation of intensity}}\right],$$

such that in each portion the mean intensity of the pixel values are determined along with the standard deviation of intensity of those pixel values in each portion. The position, size and/or shape of the area (portion) selected may affect the SNR calculation. Thus, in some embodiments, the selection of the position, size and/or shape portion(s) in which the SNR is determined may be selected based on certain factors which may take into account a variation across the image. For example, certain parts of the image may have a different SNR to other parts of the image (e.g., due to factors such as reflectivity of the skin and/or hair surface, background information and/or other features within the image). Determining the SNR for the whole image may or may not provide meaningful information for a purpose of the method described below. Determining the SNR for at least one portion of the image may provide more useful information and/or allow variations in the SNR across the image to be taken into account. However, in some embodiments, the SNR for the entire image may be determined.

Where the determined SNR is below a target SNR, the method 100 comprises, at block 106, in response to determining that the SNR is below a target SNR, causing an indication of an illumination parameter to be sent to the illumination unit to increase an amplitude modulation depth of the temporally modulated illumination used to illuminate the subject while the imaging device acquires a subsequent set of images. The subsequent set of images are used for constructing a subsequent ambient-corrected image with increased SNR for at least a portion (e.g., corresponding to the same portion of the ambient-corrected image where the SNR is determined) of the subsequent ambient-corrected image. The target SNR may refer to a SNR that allows for improving imaging in certain conditions such as where the ambient lighting conditions are not optimum or appropriate for achieving consistent and/or reliable results when performing a skin sensing measurement or analysis based on the ambient-corrected image. For example, the target SNR may refer to a threshold (e.g., a predetermined threshold) where acceptable image quality is obtained for performing a skin sensing measurement that is consistent and/or reliable. A different target SNR may be defined depending on the type of skin sensing measurement or analysis. For example, certain skin sensing measurements or analysis may need a higher SNR than other types of skin sensing measurements in order to produce consistent and/or reliable results.

As will be described in more detail, in some embodiments, a target SNR may vary depending on various factors such as the skin type under analysis. Thus, the target SNR may be selected based on various factors which may affect the skin sensing measurement or analysis performed using the ambient-corrected image.

By appropriate selection of the target SNR, the method 100 may facilitate improved imaging and/or image processing in certain conditions so that the subsequent ambient-corrected image may be a better quality for certain skin sensing measurement or analysis purposes.

Further, by providing the indication of the illumination parameter for increasing SNR for at least the portion of the subsequent ambient-corrected image, imaging may be improved.

Increasing the amplitude modulation depth may increase the SNR in the subsequent ambient-corrected image because the subsequent set of images used to construct the subsequent ambient-corrected image may each have a spatial modulation pattern with increased contrast between the maximum and minimum pixel intensity values (due to the spatial intensity modulation) in each of the subsequent set of images. By causing the increase in the amplitude modulation depth of the illumination, an ambient correcting technique that uses the different spatial intensity modulation patterns from the subsequent set of images may construct the subsequent ambient-corrected image with increased SNR (e.g., due to the difference between the maximum and minimum intensity of the illumination dominating over the ambient light so that the SNR is increased).

Certain embodiments described below refer to the indication of the illumination parameter, which may be provided in various ways in order to improve the SNR.

The SNR may, in some circumstances, be considered to play a significant role in the perceived quality of the ambient corrected images. A sufficiently high SNR may be expected to allow for accurate quantitative measurements from the ambient corrected image. For tracking of skin parameters and features over time, it may be useful that the output measurements are independent of the ambient light conditions. Sufficiently accurate tracking of the skin parameters over time may be facilitated by achieving a sufficiently high SNR in the ambient-corrected images.

Figure 2:
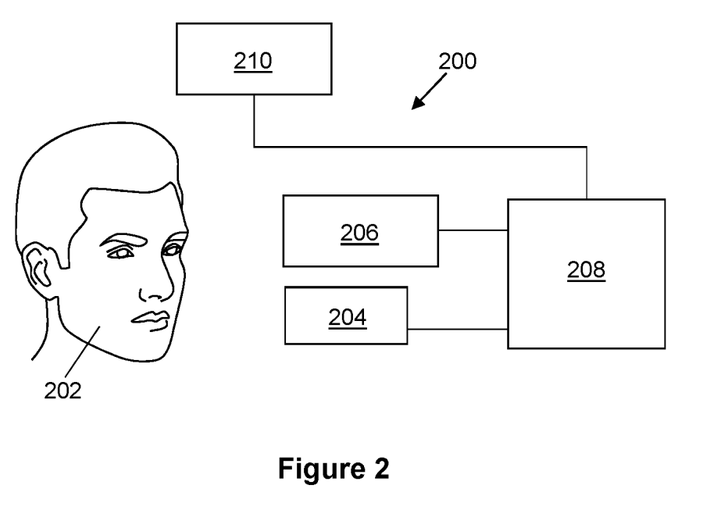
FIG. 2 is a schematic drawing of a system for improving imaging in certain conditions according to an embodiment.
Figure 5:
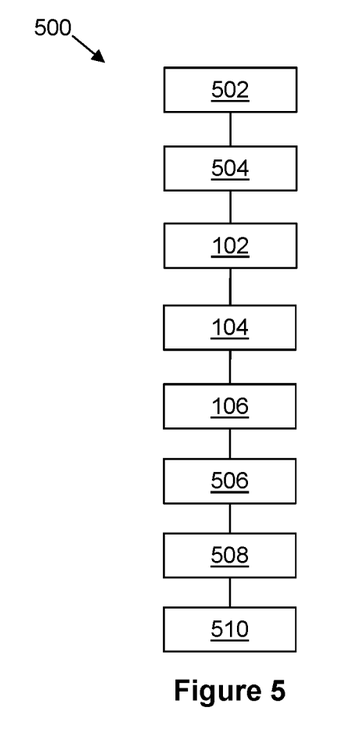
FIG. 5 refers to a method of improving imaging in certain conditions according to an embodiment.

FIG. 2 shows an example system 200 for improving imaging according to certain embodiments. The system 200 may at least partially implement certain methods described herein such as method 100 above or method 500 below. Certain blocks of the system 200 may be omitted in some embodiments.

The system 200 is used by a subject 202 and comprises an imaging system 204 and an illumination unit 206. The imaging system 204 is used to acquire the images referred to in the method 100. The illumination unit 206 is used to provide the temporally modulated illumination. The imaging system 204 and/or the illumination unit 206 may be implemented by a user device such as described above. Thus, in some embodiments, separate user devices may comprise the imaging system 204 and the illumination unit 206 and, in other embodiments, the same user device may comprise the imaging system 204 and the illumination unit 206.

In some embodiments, the imaging system 204 comprises at least one imaging device for capturing images or video (e.g., a camera in rolling shutter mode) capable of detecting a single or plurality of light sources (e.g., such as a source of ambient light and/or the illumination from the illumination unit 206) interacting with the surface (e.g., skin) of the subject 202.

The system 200 further comprises a computer 208 (e.g., comprising processing circuitry implemented by a user device or a server or cloud-based service for implementing certain methods described herein). Thus, the computer 208 may be communicatively coupled to the imaging system 204 and/or the illumination unit 206 to send and/or receive data to/from these components. This data may be processed by the processing circuitry of the computer 208 and/or be stored in a memory (e.g., of the computer 208 or accessible to processing circuitry of the computer 208). In some embodiments, the computer 208 may control the operation of the imaging system 204 and/or the illumination unit 206. In some embodiments, the computer 208 comprises a controller for controlling illumination parameters (e.g., operating parameters for the illumination unit 206) and/or detection parameters (e.g., operating parameters for the imaging system 204) and storing and/or processing the captured images or videos.

The system 200 comprises a light source 210 which may, in some embodiments, be distinct from the illumination unit 206 and provide ambient lighting for the subject 202. However, in some embodiments, the same illumination unit 206 may provide temporally modulated illumination as well as providing, or contributing to, the ambient lighting. In some embodiments, the system 200 may not comprise the light source 210. In some embodiments, the light source 210 may refer to a smart light (e.g., a smart light-emitting diode (LED) or other light source whose light output is capable of being controlled by a computer such as the computer 208). For example, some smart lights are controllable by data provided over a wireless or wired communication link e.g., to control the intensity level and/or a color output of the smart light. In this embodiment, the computer 208 is communicatively coupled to the light source 210 (e.g., to allow the computer 208 to control the output of the light source 210). In some embodiments, the computer 208 may not be capable of controlling the output of the light source 210. The light source 210 may be the sole source of ambient light or may contribute to ambient light from another source (such as the sun).

Figure 3A:
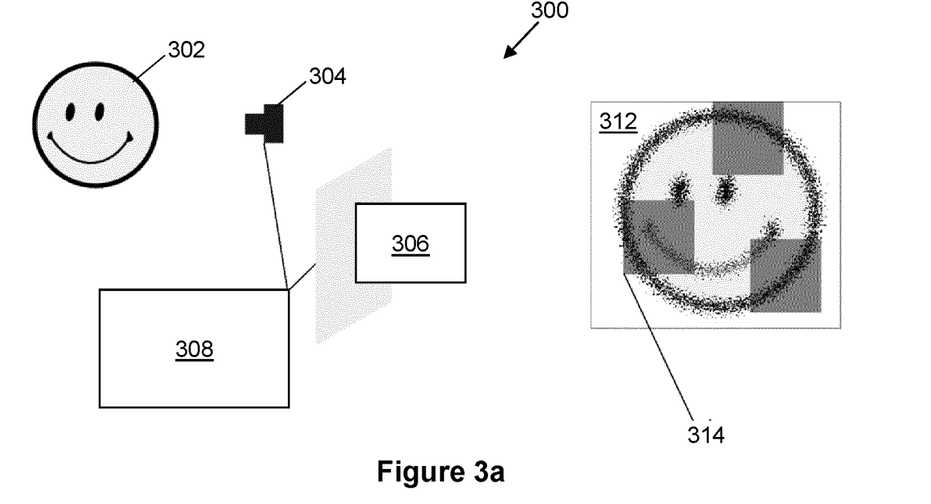
FIGS. 3a-b are schematic drawings of a system for improving imaging in certain conditions according to an embodiment.
Figure 3B:
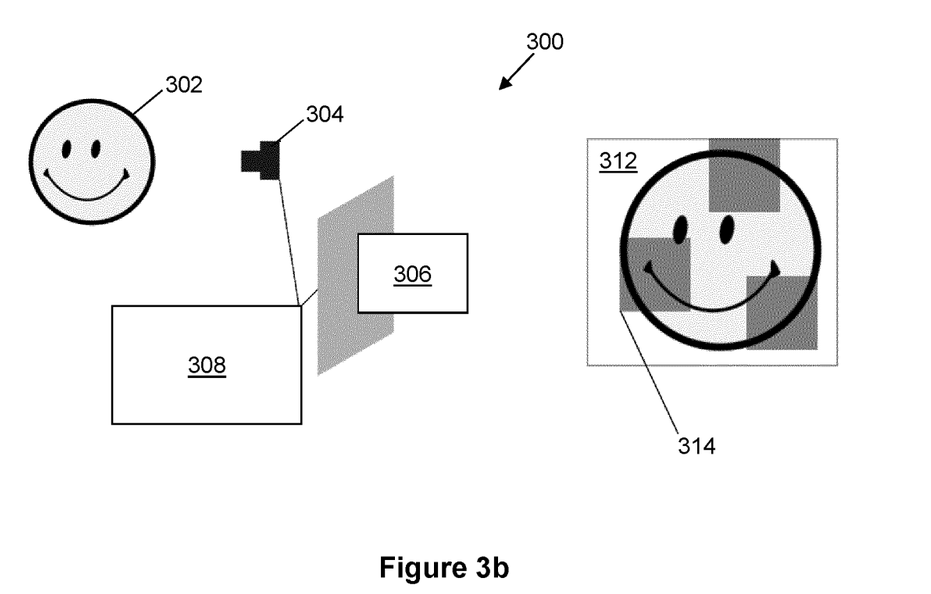

FIGS. 3a-b show a system 300 for implementing certain methods described herein, such as the method 100 of FIG. 1. The system 300 comprises certain features which correspond to certain features of the system 200 of FIG. 2 and the reference signs for these features are incremented by 100 compared with those of FIG. 2.

An imaging device 304 of the system 300 images the subject 302. The computer 308 records the average and standard deviation of the signal obtained by the imaging device 304 in terms of grey values or number of recorded photons within the integration time. The SNR is calculated using the example formula described above. In some embodiments, the SNR is calculated independently of the subject's skin type and ambient lighting conditions.

FIG. 3a shows an (ambient-corrected) image 312 of the subject 302 where the SNR for at least one portion 314 of the image 312 is determined. As can be seen in FIG. 3a, the illumination unit 306 provides a certain modulated illumination level (e.g., modulation depth, described below). However, it is apparent that in FIG. 3a, the quality of the image 312 is poor such that the at least one portion 314 of the image 312 has a poor SNR (e.g., it is 'fuzzy' or noisy).

According to certain methods described herein, the computer 308 determines that the SNR of the image 312 is not sufficiently high in FIG. 3a (i.e., it is below the target SNR) and so, in some embodiments as depicted by FIG. 3b, the computer 308 causes the illumination unit 306 to provide a different modulated illumination level (e.g., a greater modulation depth than for FIG. 3a— this is depicted by the shading adjacent the illumination unit 306 being darker in FIG. 3b than in FIG. 3a). The image 312 in FIG. 3b has a higher quality (and hence SNR) than the image 312 of FIG. 3a. The at least one portion 314 of the image 312 may reach the target SNR after at least one iteration of the method 100.

In some embodiments, the analysis of the SNR for each ambient-corrected image 312 may lead to the generation of a feedback signal for controlling the illumination unit 306 (e.g., to achieve target SNR iteratively).

A factor 'A' may be defined as the ratio of ambient light ('ambient [lux]') to the total amount of light (i.e., ('illumination+ambient [lux]') falling on the surface of the subject's skin i.e., $$A = \frac{\text{ambient } [lux]}{(\text{illumination} + \text{ambient})[lux]},$$

where the 'ambient' refers to light from a light source such as a smart light or any other light in the subject's room and/or sunlight and the 'illumination' refers to the amplitude, or modulation depth, of the temporally modulated illumination provided by the illumination unit 306.

The value 'A' may be low (e.g., A=0) when the ambient light level is zero, or much less than the amplitude of the temporally modulated illumination. This may be the case when the subject is in a dark room, out of sunlight, etc.

The value 'A' may be high (e.g., A=0.9) when the ambient light level is high, or much larger than the amplitude of the temporally modulated illumination. This may be the case when the subject is in a bright room, in bright sunlight, etc.

In other similar words, the value for the factor 'A' depends on the relative value of the ambient light level and the amplitude of the temporally modulated illumination.

In some embodiments, the A value is recorded for each image taken such that, for tracking a skin feature over time, the color information can be normalised to a specified A value.

Figure 4:
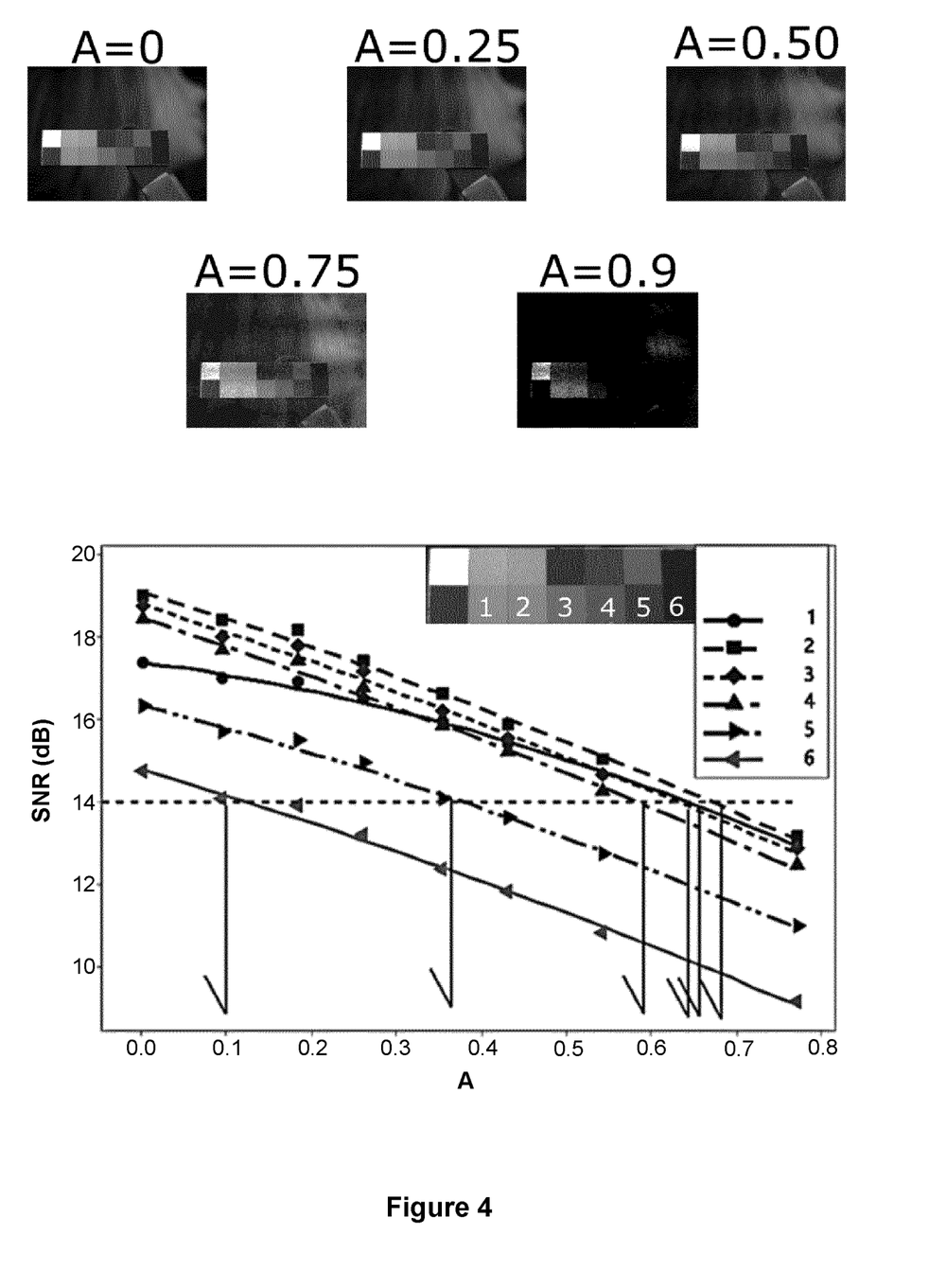
FIG. 4 shows a graph depicting the implementation of certain methods described herein according to an embodiment.

FIG. 4 contains a graph (a scatter plot of SNR (in dB) vs. A) showing the relevance of fixing the factor 'A' for obtaining a sufficient SNR in five example images of a subject (associated with the following 'A' values: 0, 0.25, 0.5, 0.75 and 0.9).

The table of blocks embedded in each image represent sampled portions of the image for different skin types (skin type patches labeled 1 to 6 in the key of the graph). The graph also shows a key with the results of SNR vs. A for the six skin types.

It can be seen that as 'A' increases, there is a visible decrease in the quality of the images. For example, the SNR appears to be relatively high for A=0 irrespective of skin type whereas the SNR appears to be relatively low (and below the target SNR in the graph) for A=0.9 for all skin types. Thus, based on the understanding of how 'A' varies according to the relative values of the ambient lighting level and the amplitude of the temporally modulated illumination, a low level of ambient light may be associated with a high SNR and a high level of ambient light may be associated with a low SNR.

As will be apparent from the image for A=0, each skin type is associated with a sufficiently high SNR (e.g., greater than a target SNR). This is depicted by the graph, which shows how the SNR for each skin type is above the target SNR (which is represented by the horizontal dashed line at 14 dB). However, for increasing values of A (associated with an increase in ambient light levels), the SNR may be reduced to below the target SNR, depending on the subject's skin type.

For example, certain skin types (e.g., for skin types labeled >4) need the factor 'A' to be less than certain other skin types (e.g., for skin types labeled≤4) in order to achieve the target SNR (i.e., 14 dB in this case). Put another way, the 'A' value may need to be much lower (e.g., 0.1) in order to achieve the target SNR for all skin types whereas the 'A' value can be higher (e.g., 0.6) for a subset of the skin types (e.g., skin types labeled <4).

Thus, as the factor 'A' increases, the image quality may degrade such that skin measurements and analysis may be compromised in scenarios where the ambient lighting is too high. This may lead to inconsistent results over time (e.g., due to the varying ambient lighting levels on different days). The degradation may be non-linear for different skin types, and hence 'A' may need to be fixed such that all targeted skin types achieve an SNR above the designed value. For example, 'A' may be set to a low value (e.g., A=0.1) so that the SNR is adequate for all skin types and performance of skin sensing measurements and analysis is acceptable. In other similar words, the factor A may be linked to the SNR according skin type so that there is a certain factor, A, that provides acceptable SNR results for all skin types.

As mentioned previously, the indication of the method 100 may lead to an improved SNR (and hence, improved skin measurements and analysis) in various ways. In order to increase the SNR or achieve the target SNR (which may be linked to a certain value of the factor, 'A'), the ambient lighting level and/or the amplitude of the temporally modulated illumination may be varied in order to achieve a specified value for the factor, A. For example, if the SNR is below the target SNR, the ambient lighting level may be reduced and/or the amplitude of the temporally modulated illumination may be increased.

Thus, in some embodiments, the target SNR is based on a skin type of the subject.

In some embodiments, the target SNR is linked to a factor, A, for which a plurality of different skin types are associated with obtaining images with at least the target SNR. The factor, A, may be defined as the ratio of ambient light level incident on the subject to a total amount of light incident on the subject. The total amount of light may refer to the combination of the ambient light level and a modulation depth of amplitude modulation provided by the illumination unit. The indication may be configured to change the modulation depth in dependence on the skin type to obtain the same factor, A, for each of the different skin types.

In some embodiments, the indication is configured to control an ambient light level for the subject to increase the SNR and/or achieve the target SNR for at least the portion of the subsequent ambient-corrected image.

In some embodiments, the indication is configured to cause a decrease in the ambient light level to increase the SNR and/or achieve the target SNR for at least the portion of the subsequent ambient-corrected image. The amplitude modulation, or 'modulation depth', may refer to the difference between the maximum and minimum amplitude of the temporally modulated illumination. In some cases, the ambient lighting level may be thought of as a 'DC', constant or slowly varying lighting level whereas the temporally modulated illumination may be thought of as an 'AC' or periodically varying illumination level.

Where the amplitude modulation depth is increased, the indication of the illumination parameter may comprise a different amplitude modulation depth to be provided by an illumination unit for providing the temporally modulated illumination. For example, if ambient lighting level is too high such that the value 'A' is too high to achieve the target SNR, the amplitude modulation depth may be increased. For example, the difference between the maximum and minimum intensity provided by the illumination unit 206 may be increased. In some cases, if the ambient lighting level decreases, it may be appropriate to decrease the amplitude modulation depth, e.g., to save energy.

In some embodiments, the indication of the illumination parameter comprises a control instruction for specifying the ambient light level to be provided by a source of the ambient light. For example, as shown by FIG. 2, the computer 208 may be communicatively coupled to the light source 210. Thus, in some embodiments, if the present SNR in the ambient-corrected image is below the target SNR, the computer 208 may cause the light source 210 to provide less light so that the value of 'A' is reduced (and hence increase the SNR to increase the SNR and/or achieve the target SNR).

In some embodiments, the indication of the illumination parameter comprises an instruction (e.g., a user instruction) to indicate (e.g., to the subject themselves or an individual/user performing measurements on the subject's skin using certain methods described herein) that a specified ambient light level is needed and/or an action (e.g., by the subject and/or user) is needed to provide or achieve the specified ambient light level. For example, if the ambient light is too high (so that A is also too high), the indication may comprise an instruction which informs a user that they need to take certain action to reduce the ambient light level. For example, the instruction may suggest an action to the subject or user, which prompts the subject to move to a darker room or reduce the ambient light levels in some other way such as switching off a light or blocking light coming into the room through a window. This instruction may be provided in the form of a prompt on a user device or user interface (e.g., a visual prompt on the device screen and/or an audible prompt from the device audio output).

Any combination of the strategies described above may be used to control the factor 'A' in order to achieve the target SNR.

FIG. 5 shows a method 500 of improving imaging in certain conditions. The method 500 comprises the blocks 102 to 106 of the method 100 and may, in some embodiments, be implemented by the computer 208. In some embodiments, certain blocks of the method 500 may be omitted and/or the blocks of the method 500 may be implemented in a different order to that shown by FIG. 5.

In some embodiments, before receiving the data corresponding to the ambient-corrected image (i.e., at block 102), an initial amplitude modulation depth of the temporally modulated illumination and/or an initial ambient light level is selected, at block 502, based on a skin type of the subject. For example, the skin type of the subject may be an initial input used in the method 500 in order to reduce the number of iterations needs to increase the SNR and/or achieve the target SNR (e.g., in some cases, multiple iterations of increasing the SNR may be needed in order to achieve the target SNR). If the system is aware of the subject's skin type in advance of implementing the method 100, the initial amplitude modulation depth may be appropriately selected to avoid performing unnecessary iterations of certain methods described herein. For example, if it is known that the user's skin type is '6' (see FIG. 4) and requires less ambient light and/or a greater amplitude modulation depth, this information may be indicated to the subject/user, the illumination unit 206 and/or the light source 210 so that the method 500 may be quicker at achieving the target SNR in the ambient-corrected image.

As referred to previously, the ambient-corrected image is determined based on a spatial intensity modulation pattern in each of a set of (e.g., consecutive) images of the subject.

Thus in some embodiments, the method 500 comprises, at block 504, causing the imaging device (e.g., of the imaging system 204) to acquire the set of images of the subject while the subject is illuminated by the temporally modulated illumination. Block 504 further comprises determining the ambient corrected image based on the set of images of the subject.

In some embodiments, the method 500 comprises, at block 506, using the indication to cause the illumination unit 206 to provide the temporally modulated illumination at the different amplitude modulation depth. For example, the indication may comprise a signal configured to cause the illumination unit 206 (e.g., a light-emitting diode or other illumination unit implemented by a user device or other appropriate device) to vary its illumination output in accordance with the signal. For example, an electrical parameter such as current and/or voltage supplied to the illumination unit 206 may be varied as a function of time in order to provide the temporally modulation illumination.

In some embodiments, the method 500 comprises, at block 508, causing the imaging device to acquire the subsequent set of images of the subject while the subject is illuminated by the temporally modulated illumination with increased amplitude modulation depth (e.g., in accordance with block 506). Block 508 further comprises determining the subsequent ambient corrected image based on the subsequent set of images of the subject.

In some embodiments, the method 500 comprises, at block 510, using the indication to control a power supply for the source (e.g., light source 210) so that the specified ambient light level is provided. For example, the power supply for the light source 210 may be configured to provide the energy to allow the light source 210 to produce the ambient light and the indication may control the amount of power (e.g., current and/or voltage) provide to the light source 210 in order to vary the light output from the light source 210.

Figure 6:
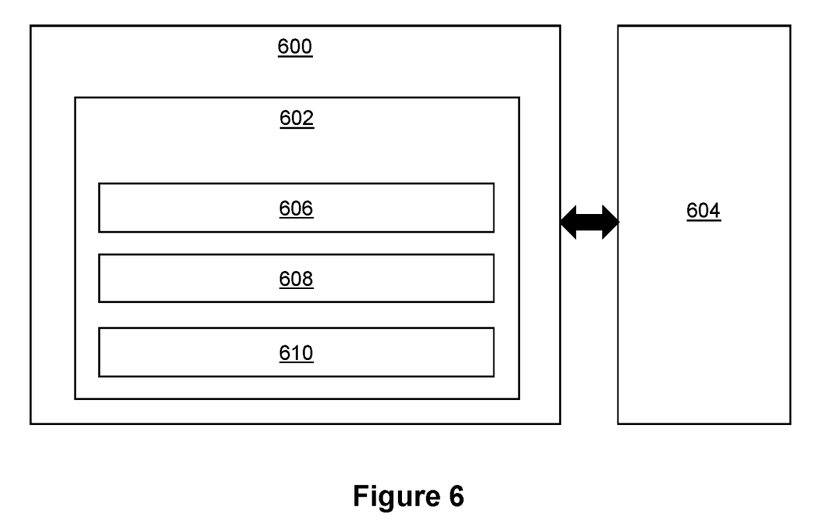
FIG. 6 is a schematic drawing of a machine-readable medium for improving imaging in certain conditions according to an embodiment.

FIG. 6 shows a tangible machine-readable medium 600 storing instructions 602 which, when executed by at least one processor 604, cause the at least one processor to implement certain methods described herein, such as method 100 or method 500.

In this embodiment, the instructions 602 comprise instructions 606 to cause the at least one processor 604 to implement block 102 of the method 100. The instructions 602 further comprise instructions 608 to cause the at least one processor 604 to implement block 104 of the method 100. The instructions 602 further comprise instructions 610 to cause the at least one processor 604 to implement block 106 of the method 100.

Figure 7:
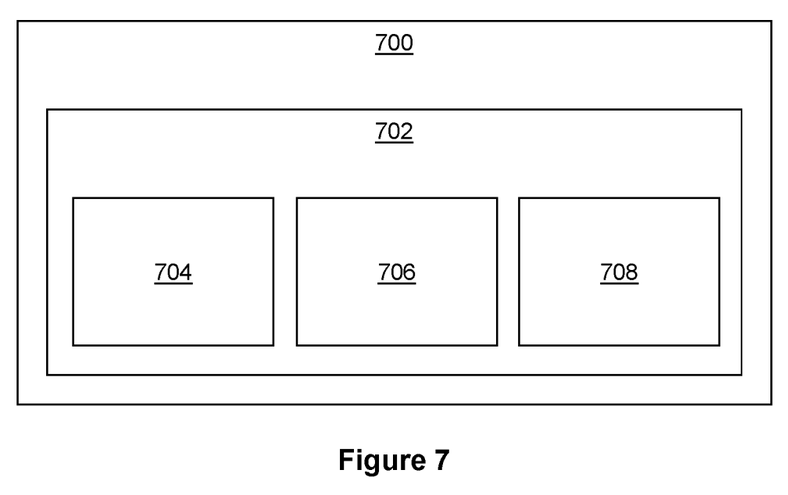
FIG. 7 is a schematic drawing of an apparatus for improving imaging in certain conditions according to an embodiment.

FIG. 7 shows an apparatus 700, which may be used for implementing certain methods described herein such as the method 100 and/or the method 500. The apparatus 700 may comprise modules with functionality corresponding to certain features described in relation to the system 200 of FIG. 2 such as the computer 208 thereof. The apparatus 700 comprises processing circuitry 702.

The processing circuitry 702 comprises a receiving module 704. The receiving module 704 is configured to receive data corresponding to an ambient-corrected image of a subject illuminated by an illumination unit (e.g., illumination unit 206) providing temporally modulated illumination with a modulation frequency that is higher than a frame acquisition rate used by an imaging device (e.g., the imaging device 204). The imaging device obtains a set of images having a different spatial intensity modulation pattern in each image due to the temporally modulated illumination and the imaging device operating in a rolling shutter mode. Information from the obtained set of images is used to construct the ambient-corrected image. The effect of ambient lighting is reduced in the ambient-corrected image.

The processing circuitry 702 further comprises a determining module 706. The determining module 706 is configured to determine a signal-to-noise ratio, SNR, of at least a portion of the ambient-corrected image.

The processing circuitry 702 further comprises an indicating module 708. The indicating module 708 is configured to cause, in response to determining that the SNR is below a target SNR, an indication of an illumination parameter to be sent to the illumination unit to increase an amplitude modulation depth of the temporally modulated illumination used to illuminate the subject while the imaging device acquires a subsequent set of images. The subsequent set of images are used for constructing a subsequent ambient-corrected image with increased SNR for at least a portion of the subsequent ambient-corrected image.

Figure 8:
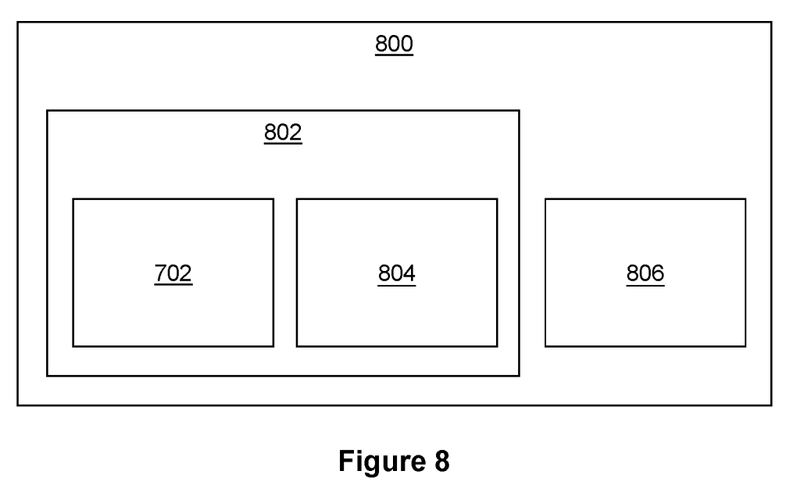
FIG. 8 is a schematic drawing of an apparatus for improving imaging in certain conditions according to an embodiment.

FIG. 8 shows an apparatus 800, which may be used for implementing certain methods described herein such as the method 100 and/or the method 500. The apparatus 800 comprises processing circuitry 802, which comprises the processing circuitry of 702 of FIG. 7.

In some embodiments, the apparatus 800 further comprises a control module 804 for controlling: the illumination unit 206 for providing the temporally modulated illumination; and/or a source of ambient light (e.g., the light source 210).

In some embodiments, the apparatus 800 further comprises a user interface 806 for providing an instruction, based on the indication of the illumination parameter, to indicate that a specified ambient light level is needed and/or a user action is needed to provide or achieve the specified ambient light level. In this embodiment, the user interface 806 is part of the apparatus 800 (e.g., if the apparatus 800 comprises a user device and the user interface 806). In some other embodiments, the user interface 806 may be a separate entity (e.g., a separate device to the computer 208 for implementing certain methods described herein).

In some cases, any of the modules described above (e.g., the receiving module 704, the determining module 706, the indicating module 708 and/or the control module 804) may comprise at least one dedicated processor (e.g., an application specific integrated circuit (ASIC) and/or field programmable gate array (FPGA), etc) for implementing the functionality of the module.

In some cases, the module above (e.g., the receiving module 704, the determining module 706, the indicating module 708 and/or the control module 804) may comprise at least one processor for implementing instructions which cause the at least one processor to implement the functionality of the module described above. In such examples, the instructions may be stored in a machine-readable medium (not shown) accessible to the at least one processor. In some examples, the module itself comprises the machine-readable medium. In some examples, the machine-readable medium may be separate to the module itself (e.g., the at least one processor of the module may be provided in communication with the machine readable medium to access the instructions stored therein).

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment. For example, the methods 100, 500 of FIG. 1 or 5 may be modified based on features described in relation to the systems 200, 300 of FIG. 2 or 3, the machine-readable medium 600 and/or the apparatus 700, 800, and vice versa.

Embodiments in the present disclosure can be provided as methods, systems or as a combination of machine-readable instructions and processing circuitry. Such machine-readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing circuitry, or a module thereof, may execute the machine readable instructions. Thus functional modules of the system 200 and/or the apparatus 700, 800 (for example, the receiving module 704, the determining module 706, the indicating module 708 and/or the control module 804) and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method comprising:
receiving data corresponding to an ambient-corrected image of a subject illuminated by an illumination unit providing temporally modulated illumination with a modulation frequency that is higher than a frame acquisition rate used by an imaging device to obtain a set of images having a different spatial intensity modulation pattern in each image due to the temporally modulated illumination and the imaging device operating in a rolling shutter mode, wherein pixel intensity information from the obtained set of images is used to construct the ambient-corrected image by determining, from the pixel intensity information, pixel intensity registered due to ambient lighting and the pixel intensity registered due to the temporally modulated illumination and constructing the ambient-corrected image based on the pixel intensity registered due to the temporally modulated illumination in the obtained set of images;

determining a signal-to-noise ratio, SNR, of at least a portion of the ambient-corrected image; and in response to determining that the SNR is below a target SNR, causing an indication of an illumination parameter to be sent to the illumination unit to increase an amplitude modulation depth of the temporally modulated illumination used to illuminate the subject while the imaging device acquires a subsequent set of images for constructing a subsequent ambient-corrected image with increased SNR for at least a portion of the subsequent ambient-corrected image.

2. The method of claim 1, wherein the target SNR is based on a skin type of the subject.

3. The method of claim 2, wherein the target SNR is linked to a factor, A, for which a plurality of different skin types are associated with obtaining images with at least the target SNR, wherein the factor, A, is defined as the ratio of ambient light level incident on the subject to a total amount of light incident on the subject, wherein the total amount of light refers to the combination of the ambient light level and a modulation depth of amplitude modulation provided by the illumination unit, and wherein the indication is configured to change the modulation depth in dependence on the skin type to obtain the same factor, A, for each of the different skin types.

4. The method of claim 1, wherein the indication is configured to control an ambient light level for the subject to increase the SNR for at least the portion of the subsequent ambient-corrected image.

5. The method of claim 1, wherein the indication is configured to cause a decrease in the ambient light level to increase the SNR for at least the portion of the subsequent ambient-corrected image.

6. The method of claim 5, wherein the indication of the illumination parameter comprises a control instruction for specifying the ambient light level to be provided by a source of the ambient light.

7. The method of claim 6, comprising using the indication to control a power supply for the source so that the specified ambient light level is provided.

8. The method of claim 1, wherein the indication of the illumination parameter comprises an instruction to indicate that a specified ambient light level is needed and/or a user action is needed to provide the specified ambient light level.

9. The method of claim 1, further comprising causing the imaging device to acquire the set of images of the subject while the subject is illuminated by the temporally modulated illumination; and determining the ambient corrected image based on the set of images of the subject.

10. The method of claim 1, further comprising causing the imaging device to acquire the subsequent set of images of the subject while the subject is illuminated by the temporally modulated illumination with increased amplitude modulation depth; and determining the subsequent ambient corrected image based on the subsequent set of images of the subject.

11. The method of claim 1, wherein, before receiving the data corresponding to the ambient-corrected image, selecting an initial amplitude modulation depth of the temporally modulated illumination and/or an initial ambient light level based on a skin type of the subject.

12. A non-transitory machine-readable medium storing instructions which, when executed by at least one processor, cause the at least one processor to implement the method according to claim 1.

13. Apparatus comprising processing circuitry, the processing circuitry comprising:

a receiving module configured to receive data corresponding to an ambient-corrected image of a subject illuminated by an illumination unit providing temporally modulated illumination with a modulation frequency that is higher than a frame acquisition rate used by an imaging device to obtain a set of images having a different spatial intensity modulation pattern in each image due to the temporally modulated illumination and the imaging device operating in a rolling shutter mode, wherein pixel intensity information from the obtained set of images is used to construct the ambient-corrected image by determining, from the pixel intensity information, pixel intensity registered due to ambient lighting and the pixel intensity registered due to the temporally modulated illumination and constructing the ambient-corrected image based on the pixel intensity registered due to the temporally modulated illumination in the obtained set of images;

a determining module configured to determine a signal-to-noise ratio, SNR, of at least a portion of the ambient-corrected image; and an indicating module configured to cause, in response to determining that the SNR is below a target SNR, an indication of an illumination parameter to be sent to the illumination unit to increase an amplitude modulation depth of the temporally modulated illumination used to illuminate the subject while the imaging device acquires a subsequent set of images for constructing a subsequent ambient-corrected image with increased SNR for at least a portion of the subsequent ambient-corrected image.

14. The apparatus of claim 13, further comprising a control module for controlling: the illumination unit for providing the temporally modulated illumination; and/or a source of ambient light.

15. The apparatus of claim 13, further comprising a user interface for providing an instruction, based on the indication of the illumination parameter, to indicate that a specified ambient light level is needed and/or a user action is needed to provide the specified ambient light level.

* * * * *